(12) United States Patent
Rudolf et al.

(10) Patent No.: US 11,780,964 B2
(45) Date of Patent: *Oct. 10, 2023

(54) PROCESS FOR THE MANUFACTURING OF A POLYMER WITH URETHANE GROUPS

(71) Applicant: BASF SE, Ludwigshafen am Rhein (DE)

(72) Inventors: Peter Rudolf, Ludwigshafen (DE); Hans-Josef Thomas, Ludwigshafen (DE); Indre Thiel, Ludwigshafen (DE); Hannes Blattmann, Cologne (DE)

(73) Assignee: BASF SE, Ludwigshafen am Rhein (DE)

( * ) Notice: Subject to any disclaimer, the term of this patent is extended or adjusted under 35 U.S.C. 154(b) by 339 days.

This patent is subject to a terminal disclaimer.

(21) Appl. No.: 16/639,204

(22) PCT Filed: Aug. 7, 2018

(86) PCT No.: PCT/EP2018/071343
§ 371 (c)(1),
(2) Date: Feb. 14, 2020

(87) PCT Pub. No.: WO2019/034473
PCT Pub. Date: Feb. 21, 2019

(65) Prior Publication Data
US 2020/0239633 A1     Jul. 30, 2020

(30) Foreign Application Priority Data

Aug. 17, 2017  (EP) ..................................... 17186544

(51) Int. Cl.
*C08G 71/04*          (2006.01)
*C07D 327/04*       (2006.01)

(52) U.S. Cl.
CPC ............ *C08G 71/04* (2013.01); *C07D 327/04* (2013.01)

(58) Field of Classification Search
None
See application file for complete search history.

(56) References Cited

U.S. PATENT DOCUMENTS

| | | | |
|---|---|---|---|
| 2,828,318 A | 3/1958 | Reynolds | |
| 3,072,676 A | 1/1963 | Johnson et al. | |
| 3,201,416 A | 8/1965 | Johnson et al. | |
| 3,349,100 A | 10/1967 | Villa | |
| 3,517,029 A | 6/1970 | Johnson | |
| 6,372,871 B1 | 4/2002 | Jimbo et al. | |
| 11,365,289 B2 * | 6/2022 | Thiel | C09D 183/10 |
| 11,384,207 B2 * | 7/2022 | Thiel | C09J 133/14 |
| 2015/0247004 A1 | 9/2015 | Lombardo et al. | |
| 2016/0122473 A1 | 5/2016 | Monnier et al. | |
| 2021/0171811 A1 * | 6/2021 | Licht | B32B 27/08 |
| 2021/0395454 A1 * | 12/2021 | Thiel | C08K 5/17 |

FOREIGN PATENT DOCUMENTS

| | | | |
|---|---|---|---|
| EP | 0 279 303 B1 | 5/1992 | |
| EP | 1134965 | 8/2003 | |
| EP | 1 506 964 A1 | 2/2005 | |
| EP | 2 468 791 A1 | 6/2012 | |
| EP | 2468791 A1 * | 6/2012 | ......... C08G 59/4064 |
| JP | H04-264075 | 9/1992 | |
| WO | WO 2011/157671 A1 | 12/2011 | |
| WO | WO 2013/144299 A1 | 10/2013 | |

OTHER PUBLICATIONS

Kulshrestha et al., "Cyclic dithiocarbonates: novel in situ gelling biomaterials," PMSE Preprints, vol. 101, (2009), STN abstract (Year: 2009).*
Kihara, N., et al., "Preparation of 1,3-Oxathiolane-2-thiones by the Reaction of Oxirane and Carbon Disulfide", The Journal of Organic Chemistry, vol. 60, Issue 2, Jan. 1, 1995, pp. 473-475.
Reynolds, et al., "Mercaptoethylation. II. Preparation of 2-Mercaptoethyl Carbamates and Oligoethylene Sulfides", The Journal of Organic Chemistry, vol. 26, Issue 12, Dec. 1, 1961, pp. 5111-5115.
International Search Report dated Nov. 6, 2018 in PCT/EP2018/071343 filed on Aug. 7, 2018.
U.S. Appl. No. 16/633,870, filed Jan. 24, 2020, Rudolf, P., et al.
U.S. Appl. No. 16/634,230, filed Jan. 27, 2020, Rudolf, P., et al.
U.S. Appl. No. 16/639,339, filed Feb. 14, 2020, Rudolf, P., et al.
Kulshrestha et al., "Cyclic Dithiocarbonates: Novel in Situ Gelling Biomaterials", American Chemical Society, 2009, 1 page.
Bingham et al., "Thiocarbonyl chemistry in polymer science", Polymer Chemistry, vol. 13, 2022, pp. 2880-2901.

(Continued)

*Primary Examiner* — Randy P Gulakowski
*Assistant Examiner* — Ha S Nguyen
(74) *Attorney, Agent, or Firm* — Grüneberg and Myers PLLC

(57) ABSTRACT

Process for the manufacturing of a polymer with urethane groups, wherein in a first alternative a compound A) with at least two five-membered cyclic monothiocarbonate groups and a compound B) with at least two amino groups, selected from primary or secondary amino groups and optionally a compound C) with at least one functional group that reacts with a group —SH are reacted or wherein in a second alternative a compound A) with at least two five-membered cyclic monothiocarbonate groups or a mixture of a compound A) with a compound A1) with one five-membered cyclic monothiocarbonate group and a compound B) with at least two amino groups, selected from primary or secondary amino groups or a compound B1) with one amino group selected from primary or secondary amino groups or mixtures of compounds B) and B1) and a compound C) with at least two functional groups that react with a group —SH or in case of a carbon-carbon triple bond as functional group that react with a group —SH, a compound C) with at least one carbon-carbon triple bond. are reacted.

20 Claims, No Drawings

(56) References Cited

OTHER PUBLICATIONS

Calo et al., "Cyclic Carbonate Formation from Carbon Dioxide and Oxiranes in Tetrabutylammonium Halides as Solvents and Catalysts", Organic Letters, vol. 4, No. 15, 2002 pp. 2561-2563.

Fan et al.' "Adaptable Strategy to Fabricate Self-Healable and Reprocessable Poly(thiourethane-urethane) Elastomers via Reversible Thiol-Isocyanate Click Chemistry", Macromolecules, vol. 53, 2020, pp. 4284-4293.

Friederichs et al., "Determination of Dithiocarbamate residues in Dietetic Foods (e.g. Ready-to-Eat Baby Food)", Application GC-6, SCA-180-006, Shimadzu Europa GmbH, Mar. 1993, 4 pages.

Kihara et al., "Catalytic Activity of Various Salts in the Reaction of 2,3-Epoxypropyl Phenyl Ether and Carbon Dioxide under Atmospheric Pressure", J. Org. Chem., vol. 58, 1993, pp. 6198-6202.

Levinn et al., "Development and Application of Carbonyl Sulfide-Based Donors for $H_2S$ Delivery", Accounts and Chemical Research, vol. 52, 2019, pp. 2723-2731.

Taguchi et al., "The Synthesis of 1,3-Dithiolan-2-ones on the Reaction of Oxiranes with Carbon Disulfide under High Pressure", Bull. Chem. Soc, Jpn., vol. 62, No. 2, 1989, pp. 474-478.

Tomita et al., "Polyaddition of Bis(cyclic theocarbonate) with Diamines. Novel Efficient Synthetic Method of Polyhydroxythiourethanes", Macromolecules, vol. 34, 2001, pp. 727-733.

Zhao et al., "Kinetic Insights into Hydrogen Sulfide ($H_2S$) Delivery from Caged-Carbonyl Sulfide (COS) Isomeric Donor Platforms", J. Am. Chem. Soc., vol. 139, No. 45, Nov. 15, 2017, 30 pages.

* cited by examiner

PROCESS FOR THE MANUFACTURING OF A POLYMER WITH URETHANE GROUPS

Object of the invention is a process for the manufacturing of a polymer with urethane groups, wherein in a first alternative a compound A) with at least two five-membered cyclic monothiocarbonate groups and a compound B) with at least two amino groups, selected from primary or secondary amino groups and optionally a compound C) with at least one functional group that reacts with a group —SH are reacted or wherein in a second alternative a compound A) with at least two five-membered cyclic monothiocarbonate groups or a mixture of a compound A) with a compound A1) with one five-membered cyclic monothiocarbonate group and a compound B) with at least two amino groups, selected from primary or secondary amino groups or a compound B1) with one amino group selected from primary or secondary amino groups or mixtures of compounds B) and B1) and a compound C) with at least two functional groups that react with a group —SH or in case of a carbon-carbon triple bond as functional group that react with a group —SH, a compound C) with at least one carbon-carbon triple bond.

are reacted.

Polyurethanes are important industrial polymers. They have very good mechanical properties and are therefore used in many technical applications. They are used, for example, as or in thermoplastics, foams or coatings. Polyurethanes are usually prepared by reacting compounds with isocyanate groups, notably diisocyanates, with diols. Compounds with isocyanate group are usually highly reactive. Such reactivity leads to increased moisture sensitivity which is problematic in some technical applications. Some compounds with isocyanate groups are considered to be harmful and may cause allergies in case of skin contact or inhalation.

There is a demand to find alternative processes for the manufacturing of polyurethanes thus avoiding the use of compounds with isocyanate groups.

WO 2013/144299 discloses radically polymerizable compounds with a cyclic five membered carbonate ring system (alkylidene-1,3-dioxolan-2-one). Urethane groups are formed by reacting these compounds or polymers thereof with amino compounds. Similar compounds are disclosed in WO 2011/157671 for the use as reactive diluents in epoxy resins. However, the synthesis of such compounds is tedious. Necessary precursors of the synthesis are not commercially available.

From EP-A 1506964 and U.S. Pat. No. 6,372,871 cyclic dithiocarbonates are known. Thiourethane groups (—NH—(C=S)—O) are obtained by reacting cyclic dithiocarbonates with amines.

Polythiourethans are not a suitable substitute for polyurethanes.

The object of EP-A 2468791 are epoxy compositions that comprise compounds with five membered cyclic ring system comprising oxygen and sulfur. The compounds used in EP-A 2468791 are dithiocarbonates. J. Org. Chem. 1995, 60, 473 to 475 which is cited in EP-A 2468791, discloses dithiocarbonates, only.

D. D. Reynolds, D. L. Fields and D. L. Johnson. Journal of Organic Chemistry, 1961, page 5111 to 5115, disclose compounds with a five membered cyclic thiocarbonate ring system and reactions thereof. Inter alia a reaction with an amino compound is mentioned.

It was an object of this invention to provide an alternative method for the manufacturing of polymers with urethane groups and to avoid the use of compounds with isocyanate groups. Furthermore, it was an object of this invention to provide hybrid polymers that comprise urethane groups, for example hybrid polymers based on epoxy resins. The polymers should be obtainable by an easy and effective manufacturing process which includes moderate temperatures, the lack of condensation by products as, for example, water or alcohol and the absence or at least reduced amount of solvents. The obtained polymers should have satisfying or even improved properties, such properties are, for example, mechanical properties, optical properties, stabilities as UV and corrosion protection. There is also an interest in polymers that have functional groups that easily undergo chemical reactions, thus allowing easy modification or crosslinking of the polymers.

Accordingly, the process described above and polymers obtainable by the process have been found.

To Compound A)

A five-membered cyclic monothiocarbonate group is a ring system with 5 members, three of them are from the monothiocarbonate —O—C(=O)—S— and the further two members are carbon atoms closing the five-membered cycle.

Compound A) may comprise, for example, up to 1000, in particular up to 500, preferably up to 100 five-membered cyclic monothiocarbonate groups.

In a preferred embodiment, compound A) comprises 2 to 10, notably 2 to 5 five-membered cyclic monothiocarbonate groups. In a most preferred embodiment compound A) comprises 2 or 3, in particular 2 five-membered cyclic monothiocarbonate groups.

Compounds A) may have, for example, a molecular weight of up to 500.000 g/mol. The latter might be the case if compound A) is a high molecular compound.

Compound A) may be a polymer or oligomer comprising a high number of five-membered cyclic monothiocarbonate groups. Such compounds A) are, for example, obtainable by polymerization or copolymerization of monomers with epoxy groups or by converting functional groups of polymers into epoxy groups and afterwards transferring the epoxy groups into five-membered cyclic monothiocarbonate groups. Further compounds A) may, for example, be polymers obtained by reacting novolacs with epichlorhydrin to obtain novolac-polyglycidylether and transferring the epoxy groups of the novolac-polyglycidylether into five-membered cyclic monothiocarbonate groups.

Preferred compounds A) have a molecular weight of up to 1000 g/mol. Most preferred are compounds C) having a molecular weight of up to 500 g/mol.

In a preferred embodiment, compounds A) do not comprise any primary or secondary amino groups and do not comprise any functional groups which react with the group —SH as listed for compound C).

In a particularly preferred embodiment compounds A) do not comprise other functional groups than monothiocarbonate groups, carboxylic ester groups or ether groups.

In a preferred embodiment compounds A) are compounds of formula I

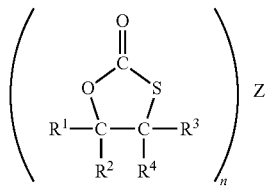

with $R^1$ to $R^4$ independently from each other representing hydrogen or an organic group with up to 50 carbon atoms whereby, alternatively, $R^2$, $R^4$ and the two carbon atoms of the monothiocarbonate group may also together form a five to ten membered carbon ring, and with one of the groups $R^1$ to $R^4$ being a linking group to Z, n representing an integral number of at least 2 and Z representing a n-valent organic group.

In case that any of $R^1$ to $R^4$ represent an organic group, such organic group is preferably an organic group with up to 30 carbon atoms. In a further preferred embodiment $R^2$ and $R^4$ do not form a five to ten membered carbon ring together with the two carbon atoms of the epoxy group.

In case that any of $R^1$ to $R^4$ represent an organic group, such organic group may comprise other elements than carbon and hydrogen. In particular, it may comprise oxygen, nitrogen, sulfur and chloride. In a preferred embodiment, the organic group may comprise oxygen or chloride. $R^1$ to $R^4$ may comprise oxygen for example in form of ether, hydroxy, aldehyde, keto or carboxy groups.

One of the groups $R^1$ to $R^4$ is the linking group to Z.

Preferably, the linking group is simply a bond or a group $CH_2$—O— or $CH_2$—O—C(=O)— or $CH_2$—$NR^{20}$— with $R^{20}$ being an aliphatic group, in particular an alkyl group with at maximum 20 carbon atoms or a group C(=O)—O— or a group $R^{21}$—C(=O)—O— wherein $R^{21}$ is an organic group, preferably a hydrocarbon group with up to 20 carbon atoms.

More preferably, the linking group is simply a bond or a group $CH_2$—O— or a group $CH_2$—O—C(=O)—.

In a most preferred embodiment, the linking group is a group $CH_2$—O—.

Preferably, two or three of the groups $R^1$ to $R^4$ in formula I are hydrogen.

In a most preferred embodiment three of the groups $R^1$ to $R^4$ represent hydrogen and the remaining group of $R^1$ to $R^4$ is the linking group to Z.

In a most preferred embodiment groups $R^1$ or $R^2$ is the linking group to Z.

n represents an integral number of at least 2. For example, n may be an integral number from 2 to 1000, in particular from 2 to 100 respectively 2 to 10, in particular 2 to 5.

In one preferred embodiment n is at least 3, preferably 3 to 5.

In a further preferred embodiment, which is the most preferred embodiment n is 2.

Z represents a n-valent organic group. In case of high number of n, such as, for example, 10 to 1000, Z may be a polymeric group, in particular a polymer-backbone, obtained, for example by polymerization or copolymerization, such as radical polymerization of ethylenically unsaturated monomers, polycondensation or polyaddition. For example, polyesters or polyamides are obtained via polycondensation under elimination of water or alcohol and polyurethanes or polyureas are obtained via polyaddition.

Such compounds of formula I are, for example, polymers obtained by radical polymerization or copolymerization of ethylenically unsaturated monomers comprising monothiocarbonate groups or of monomers comprising epoxy groups which are then transferred into a monothiocarbonate group.

In a preferred embodiment Z is a n-valent organic group with up to 50 carbon atoms, in particular up to 30 carbon atoms, and which may comprise other elements than carbon and hydrogen and n is an integral number from 2 to 5, notably 2 or 3, most preferred 2.

In a particularly preferred embodiment Z is a n-valent organic group with up to 50 carbon atoms, in particular up to 30 carbon atoms, and which comprises carbon, hydrogen and optionally oxygen, only and no further elements and n is an integral number from 2 to 5, notably 2 or 3, most preferred 2.

In a preferred embodiment Z is a polyalkoxylene group of formula G1

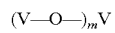

wherein V represents a C2-to C20 alkylen group and m is an integral number of at least 1. The terminal alkylene groups V are bonded to the linking group, which is one of the groups $R^1$ to $R^4$, see above.

Preferably, the C2-C20 alkylen group is a C2- to C4 alkylen group, in particular ethylene or propylene. m may, for example, be an integral number from 1 to 100, in particular from 1 to 50.

In a further preferred embodiment Z is a group of formula G2

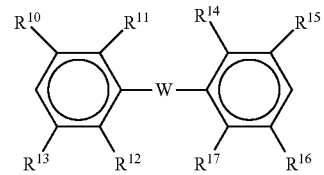

wherein W is a bi-valent organic group with at maximum 10 carbon atoms and n is 2 and $R^{10}$ to $R^{17}$ independently from each other represent H or a C1- to C4 alkyl group and wherein the two hydrogen atoms in the para position to W are replaced by the bond to the linking group, which is one of the groups $R^{1b}$ to $R^{4b}$, see above.

Preferably, at least six of $R^{10}$ to $R^{17}$ are hydrogen. In a most preferred embodiment all of $R^{10}$ to $R^{17}$ are hydrogen.

Groups W are, for example:

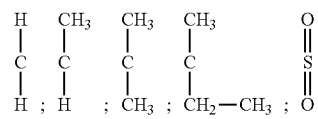

Preferably, W is an organic group that consists of carbon and hydrogen, only.

Most preferred W is

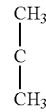

which corresponds to the structure of bisphenol A.

In a further preferred embodiment Z is a group G3, wherein G3 represents an alkylene group, notably a C2 to C8 alkylene group; preferred examples of such an alkylene group are ethylene (CH₂—CH₂), n-propylen (CH₂—CH₂—CH₂) and notably n-butylene (CH₂—CH₂—CH₂—CH₂).

Examples for preferred compounds with at least two five-membered cyclic monothiocarbonate groups are in particular those compounds which are obtained by transferring all epoxy groups of the following epoxy compounds into five-membered cyclic monothiocarbonate groups:

Non-Glycidyl Epoxides:
1,2:5,6-Diepoxyhexahydro-4,7-methanoindan, Bis (3,4-Epoxycyclohexylmethyl) Adipate, 1,4-Cyclohexanedimethanol bis(3,4-epoxycyclohexanecarboxylate, 1-Methyl-4-(2-methyloxiranyl)-7-oxabicyclo[4.1.0]heptane, 4-vinylcyclohexene dioxide, 1,2,5,6-Diepoxycyclooctane, 1,2,7,8-Diepoxyoctane, Dicyclopentadiene dioxide, epoxidized plant oils or derivatives thereof, for example soy bean oil or derivatives thereof.

Glycidylether:
Bisphenol A diglycidylether (BADGE), Hydrogenated BADGE, Glycidylether of other Di-, Tri, Tetra- and polyols such as Butandiol-d iglycidylether, Trimethylolpropan-triglycidylether, Pentaerythritol tetraglycidyl ether, Sorbitolpolyglycidylether, isosorbiddiglycidylether, Methylphenlypropandioldiglycidylether This includes also oligomeric/polymeric glycidylether such as e.g.

Polypropylenglycoldiglycidylether, Polyglycerolpolyglycidylether, novolac-glycidylether, oligomers or polymers obtained by reacting bisphenol A with an excess of epichlorhydrin.

Glycidylester:
Tetrahydrophthalic acid diglycidyl ester, Diglycidyl 1,2-cyclohexanedicarboxylate, Diglycidylorthophthalate Glycidyl amine:
N,N-Diglycidyl-4-glycidyloxyaniline, Tetraglycidylmethylenedianiline Glycidylimide:
triglycidyl isocyanurate To the Synthesis of Compound A)

Some methods for the synthesis of compounds with one monothiocarbonate group are described in the state of the art.

According to U.S. Pat. Nos. 3,072,676 and 3,201,416 ethylene monothiocarbonates may be prepared by a two-step-process. In a first step mercaptoethanol and chloro carboxylates are reacted to give hydroxyethylthiocarbonate, which is heated in the second step in a presence of metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonylsulfide. The availability of carbonylsulfide is limited. Yields and selectivities of alkylene monothiocarbonates obtained are low. M.

A synthesis using phosgene as starting material is known from U.S. Pat. No. 2,828,318. Phosgene is reacted with hydroxymercaptanes. Yields of monothiocarbonates are still low and by products from polymerization are observed.

A preferred process for the preparation of compounds A), in particular of the compound of formula I, is a process wherein a) a compound with at least two epoxy groups (shortly referred to as epoxy compound) is used as starting material b) the compound is reacted with phosgene or an alkyl chloroformate thus giving an adduct and c) the adduct is reacted with a compound comprising anionic sulfur to give the compound with at least two five-membered cyclic monothiocarbonate groups In the first process step b) the compound with at least two epoxy groups is reacted with phosgene or an alkyl chloroformate thus giving an adduct. Preferably, it is reacted with phosgene. The word phosgene shall include any phosgene substitutes; phosgene substitutes are compounds that set free phosgene. A phosgene substitute is, for example, triphosgene. Below the of reaction under the reaction under b) is shown exemplarily for a specific epoxy compound substituted by R and phosgene as reactant.

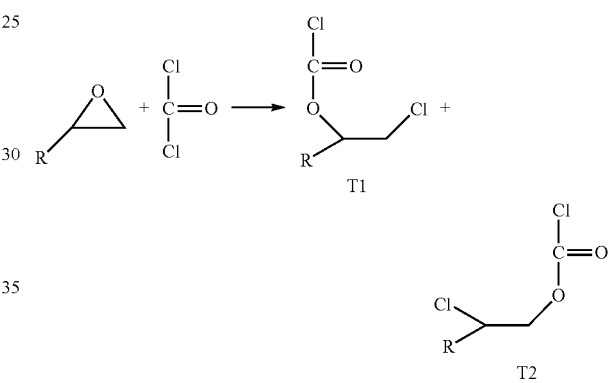

Two structural isomers of β-chloroalkyl chloroformate T1 and T2 are obtained. It is an advantage of the process that the product has a high selectivity regarding the structural isomers. In particular, at least 80%, preferably at least 90% usually at least 95% of the adduct correspond to isomer T1.

The compound with at least two epoxy groups may be reacted with phosgene or an alkyl chloroformate in any stochiometric ratio. Preferably, a very high excess of the compound with at least one epoxy group is avoided, as such a high excess would result in high amounts of unreacted starting compounds which would have to be removed during work-up of the obtained product composition.

Preferably, the phosgene, respectively chloroformate are used in an amount of 0.1 to 5 mol, in particular of 0.5 to 2 mol per mol of each epoxy group of the compound with at least two epoxy groups. In a particularly preferred embodiment the phosgene, respectively chloroformate, are used in excess.

With at least equimolar amounts of phosgene, respectively chloroformate, epoxy groups that remain unreacted can be avoided. Hence, in a preferred embodiment the phosgene, respectively chloroformate, are used in an amount of 0.9 to 5 mol, more preferably of 1 to 2 mol, in particular 1 to 1.5 mol per mol of each epoxy group of the compound with at least two epoxy groups.

The phosgene and the chloroformate are preferably a compound of formula II

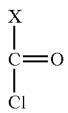

wherein X is Cl in case of phosgene or a group O—R5 with R5 representing a C1- to C4 alkyl group in case of chloroformate.

In a preferred embodiment the compound with at least two epoxy group is reacted with phosgene.

Preferably, the reaction is performed in presence of a catalyst. Suitable catalysts are salts with a quaternary ammonium cation such as tetraalkylammonium halogenides, in particular chlorides, for example tetrabutylammoniumchloride, tetrahexylammoniumchloride, benzyltributylammonium chloride order trioctylmethylammonium chloride.

Further suitable catalysts are, for example, hexa-alkylguanidinium halogenides, in particular chlorides, quarternary phosphonium halogenides, in particular chlorides, pyridine or other compounds with a ring system comprising nitrogen such as imidazole or alkylated imidazole.

Preferred catalysts are salts with a quaternary ammonium cation, in particular salts of tetra alkyl ammonium, for example tetra (n-butyl) ammonium chloride.

Preferably, the catalyst is used in an amount of 0.001 to 0.1 mol, in particular in an amount of 0.005 to 0.05 mol per mol of each epoxy group.

The phosgene or alkyl chloroformate is preferably added to the compound with at least two epoxy groups. As the reaction is exothermic, addition of phosgene or alkyl chloroformate is preferably made slowly so that the temperature of the reaction mixture is kept at the desired value. Preferably, the reaction mixture is cooled during the addition.

Preferably, the temperature of the reaction mixture is kept at −40 to 60° C., notably at 5 to 50° C.

Low molecular compounds with at least one epoxy group are usually liquid; hence, an additional solvent is not required. Preferably, a solvent is used in case of compounds with at least one epoxy group that are solid at 21° C. Suitable solvents are, in particular aprotic solvents. Suitable solvents are, for example, hydrocarbons, including aromatic hydrocarbons and chlorinated hydrocarbon.

A preferred solvent for a solid compound with epoxy groups is an additional liquid compound with epoxy groups. The liquid compound is preferably a compound with only one epoxy group. The liquid compound together with the solid compound undergo the reaction as described in process steps b) and c). The monothiocarbonate obtained from the liquid compound would usually be liquid as well and, therefore, would serve also as solvent for the most probably solid compound with at least two five-membered monothiocarbonate groups obtained from the solid compound with at least two epoxy groups.

When the reaction is completed, unreacted phosgene or chloroformate may be removed from the mixture by distillation. No further work up is necessary. The product mixture obtained comprises a compound with at least two β-chloro alkylchloroformate group. The next process step may follow immediately.

c) Second Process Step, Formation of the Monothiocarbonate Groups

Below the reaction under b) is exemplarily shown for a specific epoxy compound substituted by R and phosgene as reactant. Starting with the β-chloro alkylchlorformates formed above, the second process step c) can be exemplarily shown for $Na_2S$ as reactant as follows:

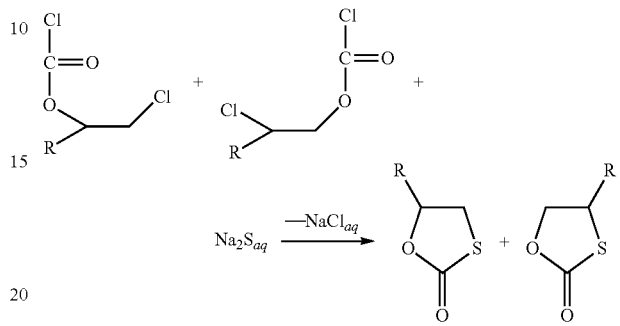

In this step the ratio of structural isomers T1 and T2 obtained in the first step and hence the selectivity is preserved.

Preferably, the product mixture obtained under b) is used under process step c) without any further work-up.

A solvent may be added in step c). Suitable solvents are, in particular, aprotic solvents. Suitable solvents are, for example, hydrocarbons, including aromatic hydrocarbons and chlorinated hydrocarbon or hydrophilic aprotic solvents, for example ethers such as tetrahydrofuran, dioxane, polyether such as glyms, acetonitrile or dimethylsulfoxid.

The product mixture from step b) is reacted with a compound comprising anionic sulfur.

The compound comprising anionic sulfur is preferably a salt.

The anionic sulfur is preferably $S^{2-}$, a polysulfide of formula $(S_p)^{2-}$ with p being an integral number from 2 to 200, preferably from 2 to 10 or $HS^{1-}$.

The cation of the salt may be any organic or inorganic cation. Preferably, it is an inorganic cation, in particular a metal. Usual metal cations are, for example, cations of alkali or earth alkali metals, such as sodium or potassium.

Preferred salts are $Na_2S$, $K_2S$, NaSH or KSH or any hydrates thereof.

The salt may be used in combination with a basic compound, in particular a metal hydroxide, such as, in particular, NaOH or KOH. Such an additional basic compound is preferably used in case of salts with $SH^-$ as anion.

The anionic sulfur may also be generated in situ, starting from sulfur or a compound comprising sulfur in non-ionic form. For example $H_2S$ may be used as source for anionic sulfur. In presence of a basic compound, for example NaOH (see above), anionic sulfur is obtained from $H_2S$ in situ.

The salt with anionic sulfur, respectively the compound from which anionic sulfur is generated in situ (together referred herein as the sulfur compound), is preferably added to the product mixture obtained in b). The sulfur compound may be added as such or, for example, as solution in a suitable solvent, such as water. In a preferred embodiment of the invention, the sulfur compound is dissolved in a solvent, in particular water, and the solution is added.

If the sulfur compound is added as solution in water, a two-phase system comprising an organic and an aqueous phase is obtained and the reaction occurs in such two-phase system. If a one phase system is desired instead, a suitable solvent may be added which acts as intermediary to combine the aqueous and organic phase to one phase again. A suitable solvent may be a hydrophilic aprotic solvent, for example a hydrophilic aprotic solvent listed above.

As the reaction is exothermic as well, addition of the salt, respectively the solution of the salt, is preferably made slowly so that the temperature of the reaction mixture is kept at the desired value. Preferably, the reaction mixture is cooled during the addition.

Preferably, the temperature of the reaction mixture is kept at −40 to 60° C., notably at −10 to 50° C.

Preferably, the salt is added in an amount of 0.5 to 2.0 mol per mol of each β-chloro alkylchlorformate group of the compound with at least two β-chloro alkylchlorformate group.

Preferably, the salt is added in an amount of 1.0 to 2.0 mol per mol of each β-chloro alkylchlorformate group of the compound with at least two β-chloro alkylchlorformate group.

In a most preferred embodiment, the salt is added in an amount of 1.0 to 1.3 mol per mol of each β-chloro alkylchlorformate group of the compound with at least two β-chloro alkylchlorformate group, as no significant excess of the salt is required to get a quick and complete reaction of all β-chloro alkylchlorformate groups.

By reaction with the salt the β-chloro alkylchlorformate groups are transferred into five-membered cyclic monothiocarbonate groups. The five-membered ring system is formed from three carbon atoms, one oxygen and one sulfur with a further oxygen double bonded to the carbon atom which is located between the oxygen and the sulfur of the ring system.

If desired, the second process step may be performed in the presence of a catalyst. Such a catalyst is, for example, a phase transfer catalyst such as ammonium salts, heterocyclic ammonium salts and phosphonium salts.

The final product obtained under c) may be worked up by extracting with a hydrophilic solvent, preferably water. In case that the above salt of anionic sulfur has been used in form an aqueous solution nor further water may be required. The organic and aqueous phase are separated. The organic phase may be washed with water which has preferably a pH of 4 to 10, in particular a pH of at least 7. The organic phase comprises the compound with at least two monothiocarbonate groups. The aqueous phase comprises unreacted sulfide/hydrogesulfide salt and/or NaCl and at least partially any catalyst added.

Any solvent may be removed from the organic phase by distillation. The obtained compound with at least two five-membered cyclic monothiocarbonate groups may be further purified by distillation or may be used without further purification.

To Compounds A1)

The five-membered cyclic monothiocarbonate A1) is a compound with one five-membered cyclic monothiocarbonate group. A five-membered cyclic monothiocarbonate group is a ring system with 5 members, three of them are from the monothiocarbonate —O—C(=O)—S— and the further two members are carbon atoms closing the five-membered cycle.

The monothiocarbonate may comprise further heteroatoms such as oxygen, sulfur, nitrogen or chloride or silicium, for example in form of functional groups selected from an epoxy group, an ether group, a hydroxy group, a keto or aldehyde or ester group, a hydroxyl group, a carboxy group, a thioether or a thiol group, or tertiary amino group or silicium functional groups. In a preferred embodiment, the monothiocarbonate has at maximum one further functional group besides the monothiocarbonate group.

The monothiocarbonate may have a molecular weight of from 104 g/mol to, for example, 100.000. The latter might be the case if the monothiocarbonate is a high molecular compound such as a polymer comprising one monothiocarbonate group, only. Preferred monothiocarbonates have a molecular weight of from 104 g/mol to 5000 g/mol. More preferred are monothiocarbonates having a molecular weight of from 104 g/mol to 1000 g/mol and most preferred are monothiocarbonates having a molecular weight of from 104 g/mol to 500 g/mol.

In a preferred embodiment compounds A1) do not comprise any primary or secondary amino groups and do not comprise any functional groups which react with the group —SH as listed for compound C).

In a particularly preferred embodiment compounds A1) do not comprise other functional groups than the monothiocarbonate group, carboxylic ester groups or ether groups.

Preferred are monothiocarbonates of formula III

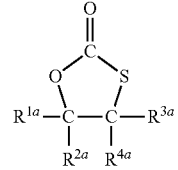

with $R^{1a}$ to $R^{4a}$ independently from each other representing hydrogen or an organic group with up to 50 carbon atoms whereby, alternatively, $R^{2a}$, $R^{4a}$ and the two carbon atoms of the thiocarbonate group may also together form a five to ten membered carbon ring In case that any of $R^{1a}$ to $R^{4a}$ represent an organic group, such organic group is preferably an organic group with up to 30, more preferably up to 20 carbon atoms carbon atoms. In a further preferred embodiment $R^{2a}$ and $R^{4a}$ do not form a five to ten membered carbon ring together with the two carbon atoms of the thiocarbonate group.

In case that any of $R^{1a}$ to $R^{4a}$ represent an organic group, such organic group may comprise heteroatoms and functional groups as listed above. In particular, it may comprise oxygen, nitrogen, sulfur, silicon and chloride. In a preferred embodiment, the organic group may comprise oxygen or chloride. $R^{1a}$ to $R^{4a}$ may comprise oxygen for example in form of ether, hydroxy, aldehyde, keto or carboxy groups. In a preferred embodiment, the organic group is an aliphatic organic group with up to 30 carbon atoms which may comprise oxygen, nitrogen or chloride, in particular oxygen.

In a more preferred embodiment, the organic group is selected from an alkyl group, from a group —CH$_2$—O—R$^{5a}$ or a group —CH$_2$—O—C(=O)—R$^{6a}$ or a group —CH$_2$—NR$^{7a}$R$^{8a}$ with R$^{5a}$ to R$^{8a}$ being an organic group with up to 30 carbon atoms, preferably up to 20 carbon atoms. In particular, R$^{5a}$ to R$^{8a}$ represent an aliphatic or aromatic group, which may comprise oxygen, for example in form of ether groups. In a preferred embodiment, R$^{5a}$ to R$^{8a}$ represent an aliphatic hydrocarbon group, such as an alkyl group with 1 to 10 carbon atoms, an alkoxy group or a poly-alkoxy group. In a most preferred embodiment, R$^{5a}$ to R$^{8a}$ represent a aliphatic hydrocarbon group, in particular an alkyl group with 1 to 10 carbon atoms.

In a most preferred embodiment, the organic group is a group —CH$_2$—O—R$^{5a}$ or a group —CH$_2$—O—C(=O)—R$^{8a}$.

Preferably, two to all four of $R^{1a}$ to $R^{4a}$ in formula III represent hydrogen and the remaining groups $R^{1a}$ to $R^{4a}$ represent an organic group.

More preferably, two and or three of $R^{1a}$ to $R^{4a}$ in formula III represent hydrogen and the remaining groups $R^{1a}$ to $R^{4a}$ represent an organic group.

Most preferably, three of $R^{1a}$ to $R^{4a}$ in formula III represent hydrogen and the remaining group of $R^1$ to $R^4$ represents an organic group. In a preferred embodiment $R^{1a}$ or $R^{2a}$ is the remaining group representing an organic group.

As preferred monothiocarbonates may be mentioned:

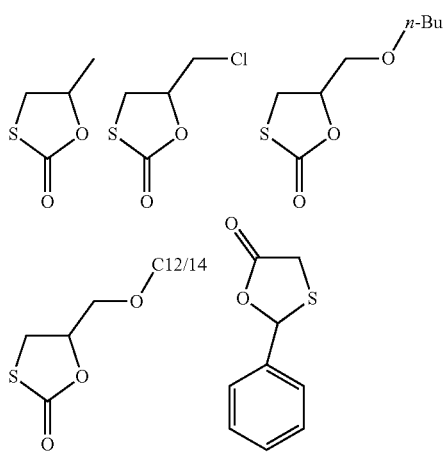

Compounds A1) may be prepared by the same process as described above for compounds A). with the only difference that a compound with one epoxy group is used as starting material.

Hence, the process for the synthesis of A1) comprises using a compound with one epoxy group as starting material
b) reacting the compound with phosgene or an alkyl chloroformate thus giving an adduct and
c) reacting the adduct with a compound comprising anionic sulfur to give the compound with one five-membered cyclic monothiocarbonate group.

Further details of the process described above for compounds A) apply also to the process for the synthesis of A1).

To Compound B)

Compound B) is a compound with at least two amino groups, selected from primary or secondary amino groups. In this patent application the word amino group shall mean a primary or secondary amino group if not indicated otherwise or obvious from the content otherwise.

Compound B) may have, for example, a molecular weight of up to 500.000 g/mol. The latter might be the case if compound B) is a high molecular compound such as a polymer comprising amino groups.

Preferred compounds B) have a molecular weight of up to 1000 g/mol. Most preferred are compounds B) having a molecular weight of from 60 g/mol to 500 g/mol.

In a preferred embodiment compounds B) do not comprise any monothiocarbonate groups and do not comprise any functional groups which react with the group —SH as listed for compound C).

In a particularly preferred embodiment compounds B) do not comprise other functional groups than primary or secondary amino groups, carboxylic ester groups or ether groups.

Compounds B) may have, for example, up to 1000 amino groups, in particular up 500 and preferably up to 100 amino groups. A high number of amino groups which may be the case with polymeric compounds B) such as linear or branched polyvinylamine or polyethylenimine or polylysin.

In a preferred embodiment compound B) comprises 2 to 10 amino groups, preferably 2 or 3 amino groups and, in a most preferred embodiment compound B) comprises 2 amino groups.

In a preferred embodiment, at least one of the amino groups is a primary amino group.

In a particularly preferred embodiment at least two of the amino groups are primary amino groups.

In a most preferred embodiment compound B) is a compound with two primary amino groups.

Suitable Compounds B) are for Example

Alkylendiamines or alkylenpolyamines such as ethylenediamine, propylenediamine, butylene diamine, pentamethylene diamine, hexamethylene diamine, neopentanediamine, octamethylendiamine, 1,3 diaminopentane, 2-Methylpentan-1,5-diamin Alkylendiamines or alkylenpolyamines comprising ether groups (polyetheramine) such as such polyglycoldiamine, oxypropylene diamine or polyoxypropylene diamine.

Amino acids with two amino groups are, for example, lysin and orhithin.

Other diamines are, for example, 4,7,10 Trioxatridecane-1,13-diamine, 4,9-dioxadodecane-1,12-diamine, 3,6-dioxa-1, 8-octane diamine, 4,7-dioxa-1, 10-decanediamine, or aminoethylethanolamine.

cycloaliphatic diamines, such as cyclohexyldiamines, for example 1,2 diaminocyclohexane, 1-methyl-2,4-diaminocyclohexane, 1-methyl-2,6-diaminocyclohexane or mixtures thereof, isophorone diamine, bis(4-amino-cyclohexyl)methane, 1,3-bis(aminomethyl)cyclohexane, 1,4-bis(aminomethyl)cyclohexane, 2,5-bisaminomethyl tetrahydrofuran, 3,3"-Dimethyl-4,4"diamino-dicyclohexylmethane aromatic diamines such as 1,2-phenylendiamine or 1,4 phenylendiamine, toluene diamines, 4,4' diamino-diphenylmethane, 4,4' diaminodiphenylsulfone, 2,5-bisaminomethyl furan, amino compounds with primary and secondary amino groups such as N-aminoethylpiperazine, dialkylentriamines or polyalkylentriamines, for example diethylenetriamine or triethylenetetramine, dipropylene triamine, N,N-Bis-(3-aminopropyl)methylamine, fatty diamines Further compounds B) with more than two amino groups are for, example Polyimin, polyvinylamin, polyallylamine, polylysine, polyetheramines based on TMP, Di-TMP, glycerol, pentaerythrit, polyglyerol, glucosamine, epoxy-amines (from molar excess of diaminocompounds+epoxy resin), 3-(2-Aminoethyl)-1,5-pentanediamine, 3,3',3"-Triaminotripropylamine, polyamidoamines, aminoalkyl melamine, amino functionalized inorganic hybrid materials such as e.g. metal organic frameworks.

Compounds B may also be used in a form wherein the amino groups are protected with a protecting group. As soon as it become necessary or desired the protecting group is removed so that the compounds B) above with free amino groups are obtained. Usually, removal of the protecting groups occurs under the conditions of the reaction. Usual protected amino groups for amino groups are, for example, ketamine, aldimine, imidazolidine, oxazolidine, lewis acid complexed amines, carbamates, benzyloxycarbonyl amines, acyloximes, formanilidine. The deprotecting reaction can, for example, be triggered by either temperature, light, pH or presence of water/humidity.

To Compound B1)

Compounds B1) are compounds with only one amino group which is either a primary or a secondary amino group.

Preferably, it is a primary amino group.

Preferred compounds B1) have a molecular weight of at maximum 1000 g/mol, in particular of at maximum 500 g/mol.

In a preferred embodiment compounds B1) do not comprise any monothiocarbonate groups and do not comprise any functional groups which react with the group —SH as listed for compound C).

In a particularly preferred embodiment compounds B1) do not comprise other functional groups than primary or secondary amino groups, carboxylic ester groups or ether groups.

Compounds B1 are, for example, monoalkylamines with a primary amino group such as C1 to C20 alkylamines or cycloalkyl amines or etheramines such as 2-methoxyethylamine or 3-methoxypropylamine or di- or polyether amines such as di- or polyglycol amine, polyoxypropylene amine.

Compounds B1 may comprise also tertiary amino groups such as (dimethyl amino)propylamine, 3-(diethyl amino) propyl amine, 2-(diethylamino) ethylamine Compounds B1 may comprise functional groups that are not reactive with —SH, such as carbon acid groups or hydroxy groups or silyl groups.

Compounds B1 with silyl groups are, for example, (trialkoxysilyl)alkyl amines. A compound B1 with a sulfonic acid group is taurine.

Amino alcohols are, for example, ethanoamine, isopropanolamine, ethylethanolamine, 2-(2-aminoethoxy)ethanol, 3-amino-1-propanol, 5-amino-1-propanol, hydroxyethyl piperazine.

To Compound C)

Compounds C) comprises at least one functional group that reacts with a group —SH in case of the first alternative and at least two functional groups that react with a group —SH in case of the second alternative. The following disclosure regarding the nature of the functional group applies to both alternatives.

Compounds C) may have, for example, a molecular weight of up to 500.000 g/mol. The latter might be the case if compound C) is a high molecular compound such as a polymer comprising functional groups that react with a group —SH.

Preferred compounds C) have a molecular weight of up to 1000 g/mol. Most preferred are compounds C) having a molecular weight of from 60 g/mol to 500 g/mol.

Compounds C) may have, for example, up to 1000 functional groups that react with a group —SH, in particular up 500 and preferably up to 100 functional groups that react with a group —SH.

In a preferred embodiment compound C) comprises 2 to 10 functional groups that react with a group —SH.

In a most preferred embodiment compound C) comprises 2 or 3 functional groups that react with a group —SH.

In a preferred embodiment, the reaction of the functional group of compound C) with the group —SH results in the formation of a sulfur-carbon bond.

The reaction of the functional group of C) with the group —SH may be an addition reaction, a condensation reaction or a nucleophilic substitution reaction.

Compounds C), that undergo an addition reaction with the group —SH are, for example, compounds with non-aromatic, ethylenically unsaturated groups or compounds with epoxy groups or compounds with isocyanate groups as functional groups. Non-aromatic, ethylenically unsaturated groups are non-aromatic carbon-carbon double bonds or carbon-carbon triple bonds.

A triple bond may react twice with —SH. In a first reaction, an —SH group may undergo an addition reaction to the triple bond whereby the triple bond becomes a double bond. The double bond formed may react with a further group —SH. Hence one triple bond is equivalent to two functional groups that react with a group —SH.

Compounds C), that undergo a condensation reaction with the group —SH are, for example, compound with carbonyl groups as functional group, for example mono carbonyl compounds or dicarbonyl compounds such as dialdehydes or diketones.

Compounds C), that undergo a nucleophilic substitution reaction with the group —SH are, for example, compounds with an halide, in particular chloride, as functional group.

In a preferred embodiment compounds C) do not comprise primary or secondary amino groups and do not comprise monothiocarbonate groups.

In a particularly preferred embodiment compounds C) do not comprise other functional groups than functional groups selected from the functional groups which react with the group —SH, carboxylic ester groups or ether groups.

Preferably, the functional groups of compound C) that react with —SH are selected from nonaromatic, ethylenically unsaturated groups, epoxy groups, isocyanate groups, groups with a non-aromatic carbon-nitrogen double bond, carbonyl groups or halides.

More preferably, the functional groups of compound C) that react with —SH are selected from non-aromatic, ethylenically unsaturated groups or epoxy groups.

Most preferably, the functional groups of compound C) that react with —SH are non-aromatic, ethylenically unsaturated groups.

In one particularly preferred embodiment of the invention, the functional groups of compound C) that react with —SH are methacryl groups.

In one embodiment of the invention epoxy groups are excluded as functional groups of compound C) that react with —SH.

To compounds C) with ethylenically unsaturated groups as functional groups.

Compounds C) having one unsaturated group herein are referred to as monomers and compounds C) having at least two unsaturated groups herein are referred to as oligomers such oligomers preferably comprise 2 to 10, in particular 2 or 3 unsaturated groups.

Compounds C) with unsaturated groups selected from non-aromatic carbon-carbon double bonds or triple bonds are preferably polymerizable by a radical, cationic or an anionic polymerization mechanism.

In a preferred embodiment the unsaturated groups of compound C) are non-aromatic carbon-carbon double bonds.

Preferred compounds C) are those wherein the non-aromatic carbon-carbon double bond is a vinyl group $CH_2=CH—$; a vinylene group $—CH=CH—$, an unsaturated carbonyl group $CH_2=CRC(=O)—$ with R=H, alkyl; an acryl group $CH_2=CH—C(=O)—O—$; a methacryl group $CH_2=C(CH_3)C(=O)—O$, an acrylamide group $CH_2=CH—C(=O)—N$, or a cyanacryl-group $CH_2=C(CN)—C(=O)—O$, or an methylenmalonate-group $CH_2=C[—C(=O)—O]_2$ or an vinylene 1,3 dicarbonyl group $CH_2=C[—C(=O)—]_2$ or a 1,4 dicarboxyalkylene group $—O(O=)C—CH=CH—C(=O)O—]$, an allyl group CH$_2$=CHCH$_2$—, especially allylethers CH$_2$=CH—CH$_2$—O— or a maleimide group or a crotonyl group.

Preferred monomers are acrylic or methacrylic compounds, vinylesters, for example vinyl acetate, vinyl ethers, vinyl lactames, for example N-vinyl pyrrolidone, vinyl aromatics as styrene, vinyl halides as vinyl chloride or vinyl fluoride or olefines with one carbon-carbon double bond, such as ethylene, propylene.

In the following the term "(meth)acryl" is used. The term "(Meth)acryl" denominates an acryl group or methacryl group and a (meth) acryl compound is a compound comprising acryl groups or methacryl groups or both.

Particularly preferred are monomers with an acrylic or methacrylic compounds or vinylether. Acrylic or methacrylic compounds are, for example (meth)acrylic esters, in particular alkyl or hydroxyalkyl (meth)acrylates, (meth)acryl nitrile, or (meth)acrylic acid. Vinyl ether are for example vinyl alkyl ether.

Compounds C with a triple bond are, for example alkynes, such as acetylene or propyne, mixtures of propyne/allene or propargyl alcohol, ethers of propargyl alcohol.
or esters of propargyl alcohol.

Preferred oligomers are in particular compounds with at least two acrylic or methacrylic groups, at least two vinyl groups or olefines with at least two carbon-carbon double bonds, unsaturated polyesters or cyanaurates or isocyanurates which are substituted by at least two unsaturated groups.

Olefins with two carbon-carbon double bonds are, for example, butadiene, cyclooctadiene, cyclododecatriene, isoprene, limonene, divinyl cyclohexane or poybutadiene or polyisoprene.

Oligomers with at least two acrylic or methacrylic groups are in particular (meth)acrylic esters of polyfunctional alcohols or of alkoxylated polyfunctional alcohols.
Examples of such alcohols are bifunctional alcohols, such as ethylene glycol, diethylene glycol, triethylene glycol, propylene glycol, dipropylene glycol, tripropylene glycol, butanediol, pentanediol, hexanediol, neopentyl glycol, alkoxylated phenolic compounds, such as ethoxylated or propoxylated bisphenols, cyclohexanedimethanol, trifunctional and higher-functional alcohols, such as glycerol, trimethylolpropane, butanetriol, trimethylolethane, pentaerythritol, ditrimethylolpropane, dipentaerythritol, sorbitol, mannitol and the corresponding alkoxylated, in particular ethoxylated and propoxylated, alcohols.

(Meth)acrylic esters of polyesterols may also be mentioned as oligomers.

Suitable polyesterols are, for example, those which can be prepared by esterification of polycarboxylic acids, preferably dicarboxylic acids, with polyols, preferably diols. The starting materials for such polyesters containing hydroxyl groups are known to the person skilled in the art. Preferably used dicarboxylic acids are succinic acid, glutaric acid, adipic acid, sebacic acid, o-phthalic acid, the isomers and hydrogenation products thereof and esterifiable derivatives, such as anhydrides or dialkyl esters of said acids. Maleic acid, fumaric acid, tetrahydrophthalic acid or the anhydrides thereof are also suitable. Suitable polyols are the above mentioned alcohols, preferably ethylene glycol, 1,2- and 1,3-propylene glycol, butane-1,4-diol, hexane-1,6-diol, neopentyl glycol, cyclohexanedimethanol and polyglycols of the ethylene glycol and propylene glycol type.

(Meth)acrylates of polyesterols can be prepared in a plurality of stages or in one stage, as described, for example, in EP 279 303, from acrylic acid, polycarboxylic acid and polyol.

Epoxide (meth)acrylates or urethane (meth)acrylates may also be suitable oligomers.

Epoxide (meth)acrylates are, for example, those which are obtainable by reacting epoxidized olefins or poly- or mono- or diglycidyl ethers, such as bisphenol A diglycidyl ether, with (meth)acrylic acid.

The reaction is known to the person skilled in the art and is described, for example, in R. Holmann, U.V. and E.B. Curing Formulation for Printing Inks and Paints, London 1984.

Urethane (meth)acrylates are in particular reaction products of hydroxyalkyl (meth)acrylates with poly- or diisocyanates (cf. also R. Holmann, U.V. and E.B. Curing Formulation for Printing Inks and Paints, London 1984).

Further oligomers are, for example, low molecular weight unsaturated polyesters which in particular have double bonds as a result of a content of maleic acid, fumaric acid or itaconic acid.

Oligomers with at least two vinyl groups are, for example divinylether such as diethylenglycol- or triethylenglycol-divinylether.

Further oligomers are, for example
divinyl sulfon, or

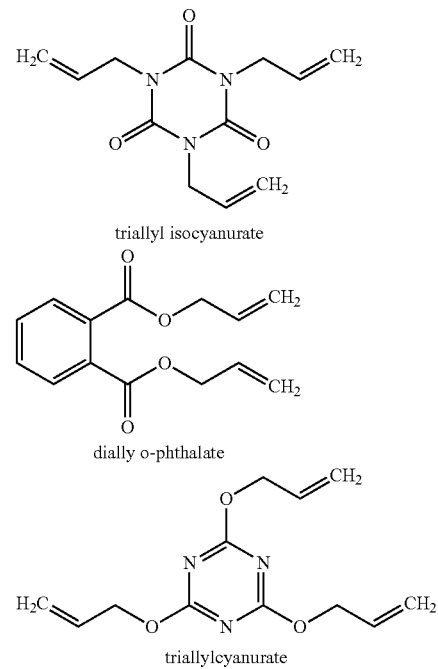

triallyl isocyanurate dially o-phthalate triallylcyanurate

In a preferred embodiment, compounds C) with ethylenically unsaturated groups as —SH reactive group are acrylic or methacrylic compounds, in particular (meth)acrylates of polyfunctional alcohols, or compounds with vinyl ether groups or unsaturated polyester. In a particularly preferred embodiment compounds C) with ethylenically unsaturated groups as —SH reactive groups are methacrylic compounds. To compounds C) with epoxy groups as functional groups Compounds C) with at least one epoxy group are for example, compounds obtained by reacting the compounds with at least one alcohol groups with epichlorohydrin.

Compounds C) with one epoxy group are, for example, epichlorohydrin or derivatives thereof wherein the chloride of epichlorohydrin is replaced by a hydroxy group (glycidol)

ether group (glycidyl ether), ester group (glycidyl ester) or amino group (glycidyl amine).

Examples of compound C with at least two epoxy groups which may be mentioned are the diglycidyl ethers of bisphenol A or bisphenol F or bisphenol S and the diglycidylethers of hydrogenated bisphenol A or bisphenol F or diglycidylethers of aliphatic diols such as diglycidylethers of polyalkoxylene diols. Mentioned may be also oligoglycidylether based on oligoalcohols. Examples are also epoxy resins which are obtainable by using the compounds with at least two alcohol groups in excess compared to the epichlorhydrin. In such epoxy resins the degree of polymerization of the compound with at least two alcohol groups is preferably from 2 to 25, in particular from 2 to 10.

Further examples are epoxidized fatty acid, fatty acid ester or fatty acid alcohol which have at least two epoxy groups.

Other compounds with at least two epoxy groups are, for example, tetraglycidylmethylenedianiline (TGMDA), triglycidylaminophenol and triglycidylisocyanurate, see below

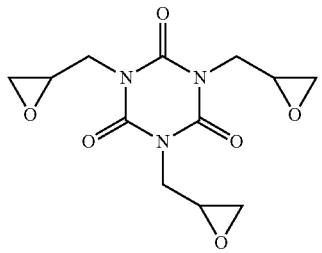 [SMILES: O=c1n(CC2CO2)c(=O)n(CC2CO2)c(=O)n1CC1CO1]

Other compounds C) with more than one epoxy group may be obtained by polymerization or copolymerization of glycidyl (meth)acrylate or of glycidyl vinylether.

To Compounds C) with Isocyanate Groups as Functional Groups

Compounds C) with isocyanate groups as functional groups are monoisocyanates, diisocyanates and polyisocyanates with at least three isocyanate groups.

Monoisocyanate, diisocyanates or polyisocyanates may be aliphatic, cycloaliphatic or aromatic compounds.

Diisocyanates are, for example, 2,2'-, 2,4'- and 4,4'-diphenylmethane diisocyanate, isophoron diisocyanate, 2,4- or 2,6-toluylen diisocyanate (TDI), tetramethylen diisocyanate, hexamethylene diisocyanate (HDI), naphtylen diisocyanate or uretdiones of diisocyanates.

Polyisocyanates are, for example, isocyanurates of diisocyanates.

Diisocyanates or polyisocyanate may also be prepolymers obtained by reacting the above di- and polyisocyanates with polyols having at least two hydroxy groups or polyamines having at least two amino groups selected from primary or secondary amino groups.

To Compounds C) with Different Functional Groups

Compound C) may have different functional groups that react with —SH, for example one epoxy group and one (meth)acryl group. Such compounds are, for example, vinyl (meth)acrylate, allyl (meth)acrylate, glycidyl (meth)acrylate or allyl glycidyl ether or polymeric compounds comprising different functional groups.

To the synthesis of the polymer with urethane groups.

The principles of the reaction of A) with B) and optionally C) according to the first alternative are in the following described for a compound A) with two cyclic monothiocarbonate groups and a compound B) with two amino groups:

Each cyclic monothiocarbonate group of A) is opened by reaction of A) with an amino group of compound B). As A) has two monothiocarbonate groups and B) has two amino groups the reaction is a polyaddition resulting in a polymer of A) and B).

This polyaddition is exemplarily shown below for a specific compound A) and B).

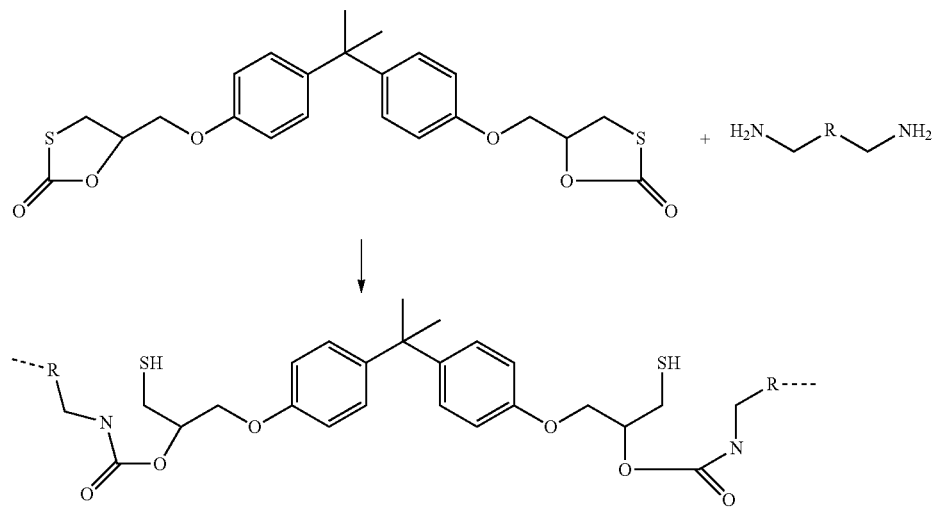

In the above example a polymer is formed which has urethane groups and —SH groups.

If desired, the —SH groups may be further reacted. The —SH group is highly reactive and readily reacts with the reactive groups of compound C). With a compound C) having more than one reactive group a crosslinked polymer is obtained. With a compound C) having one reactive group a polymer of A) and B) with side groups of C) is obtained.

Without the addition of compound C), the —SH groups may oxidize and will form disulfide bridges. Such oxidation may occur at room temperature in the presence of oxygen.

The polymer of A) and B) or the polymer of A), B) and C) typically comprises structural elements of formula IV

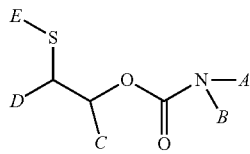

The variables A to E represent substitutions by any substituents.

The typical structural element is a urethane group with a sulfur atom being bonded via an ethylene group to the oxygen of the urethane group.

In the second alternative compound C) has at least two functional groups that react with a group —SH. A triple bond as functional group corresponds to two functional groups as the triple bond reacts twice; the first reaction with —SH leads to a double bond which then reacts again with —SH.

Due to compound C) having at least two functional groups that react with —SH, the number of functional groups of compounds A) and B) may be reduced. Hence, therefore, compound A) may be used in admixture with compounds A1) having only one cyclic monothiocarbonate and/or compound B) may even be replaced by a compound B1) having one amino group, only. Compound B1) undergoes the ring opening reaction with A) as described above; hence setting free one group —SH from each cyclic monothiocarbonate group. The —SH groups react with compound C) thus building up a polymer chain or network.

In both alternatives, the reaction may be carried out in one step or two steps.

A one-step reaction means that all compounds are reacted simultaneously. In the first alternative, A) and B and optionally C) are reacted simultaneously. In the second alternative, all compounds A), A1), B), B1) and C) are reacted simultaneously.

In a two-step reaction, the cyclic monothiocarbonate groups undergo the ring opening reactions of with the amino groups separately in a first step, followed by the reaction of the —SH groups of the obtained intermediate with the reactive groups of C).

In case of the first alternative, a two-step reaction is possible, if C) is used, only.

Hence, a two-step reaction is carried out in the first alternative by first reacting A) and B) and then reacting the obtained intermediate with C) and in the second alternative by first reacting A) or mixtures of A) and A1) and B) or B1) or mixtures of B) and B1) and then reacting the obtained intermediate product with C).

A polymer with urethane groups is obtainable by the process, regardless whether the reaction is carried out in one step or two steps. The polymer comprises the urethane groups in form of the structural element of formula IV.

Preferably, the polymer obtainable by the process has a content of structural elements of formula IV of 0.0001 to 0.3 mol, notably of 0.001 to 0.2 mol per 100 g of polymer, whereby the structural element of formula IV is calculated to have a molecular weight of $3 \times 12 + 2 \times 16 + 14 + 32 = 114$ g/mol, which is the sum of the molecular weight of all atoms C, O, N and S in formula IV.

The stoichiometry of the two-step reaction is as follows: One monothiocarbonate group of A) or A1) reacts with one amino group of B) or B1) resulting in one —SH group reacting with one reactive group of C) resulting in a stoichiometry of Monothiocarbonate groups: amino groups: groups reactive with —SH of 1:1:1

In calculating the stoichiometric amounts of A), B) and C) it has to be considered that A), B) and C) may comprise 2 or more than 2 monothiocarbonate, amino or —SH reactive groups.

Preferably, a large excess of any compound is avoided and any of compounds A), A1) B), B1) and C) are used in an amount that deviates not more than 50%, respectively not more than 20% from the equimolar amounts corresponding to the stoichiometry of the reactions.

In case of a one-step reaction it has to be considered that some compounds C) would/could react also with amino groups of B) thus reducing the availability amino groups for the ring-opening reaction. It has to be distinguished between following cases:

Case 1

If the reactivity of the monothiocarbonate groups of A) respectively A1) with the amino groups of B), respectively B1) is much higher than the reactivity of compound C) with the amino groups of B and/or B1), the stoichiometry and the result of the one-step reaction corresponds to the result of the two-step reaction as A), respectively A1) and B), respectively B1) will react first, followed by the reaction of the obtained intermediate with C).

Case 2

If the reactivity of compound A), A1) and of compound C) with the amino groups of B), B1) is in the same order of magnitude, a one-step reaction will result in a hybrid polymer comprising urethane groups.

Case 3

In case that the reactivity of compound A), A1) with the amino groups of B), B1)) is much lower than the reactivity of compound C) with the amino groups of B), B1), the result of the one-step reaction may be a polymer with low amount of urethane groups.

The further disclosure relates to specific compounds C):

To the synthesis with compounds C) having at least two epoxy groups

This is usually a Case 2. The reactivity of epoxy groups of C) with amino groups of B), B1) is usually similar to the reactivity of compound A) with the amino groups of B). In the one-step reaction of all three components, there will be competing reactions of the amino groups of compound B), B1) with either compound A), A1) (ring-opening of the monothiocarbonate) or compound C) (crosslinking/chain extension of epoxy compounds with amino compounds). As product of this one-step reaction a hybrid polymer is obtained. The molar ratio of the compounds A)

A1), B), B1) and C) determines the nature of the hybrid polymer. With minor amounts of compound A), A1) the hybrid polymer obtained corresponds to an epoxy resin which is modified with urethane groups. The obtained urethane-modified epoxy resins have improved application properties and combines the benefits of epoxy resins with those resulting from the content of urethane groups.

The one step reaction with compounds C) being a compound with at least at least two epoxy groups is one embodiment of the invention. In this embodiment, the molar ratio of compounds A) to the moles of epoxy groups of C) is from 1:100 to 100:1. More preferred is a ratio compounds A) to the moles of epoxy groups of C) of 50:1 to 1:50.

Preferably, compounds C with at least two epoxy groups are reacted according to the two-step reaction described above, this applies to both alternatives of the process claimed.

To the synthesis with compounds C) having at least two methacrylic groups as unsaturated groups These systems usually follow Case 1 since aza-Michael addition of amines towards methacrylates are considered unfavorable while addition of mercaptanes can proceed at low temperature. Such behavior is described in (Polymer preprints 2010, 51, 281)

To the synthesis with compounds C) having at least two acrylic groups as unsaturated groups These systems usually follow Case 3.

It is known in literature that aza-Michael addition reaction with acrylates can be suppressed under certain reaction conditions (solvent dependence). Depending on the resulting kinetics of the aza-Michael addition the overall system can subsequently also follow Case 2 or even Case 1.

To the synthesis with compounds C) having other unsaturated groups than (meth) acrylic groups.

These systems usually follow Case 1. Addition of —SH to the unsaturated group of compound C can preferably be achieved via radical reaction. Radical reaction can be thermally catalyzed and/or photoinitiated.

To the synthesis with compounds C) having at least two isocyanate groups as unsaturated groups This is a Case 3. A one step reaction is not preferred.

General Issues Regarding the Process

The following disclosure applies to both alternatives of the process if not stated otherwise.

In case of the first alternative and a one-step reaction, compounds A), B) and optionally C) may be mixed to obtain a curable mixture comprising a compound A) with at least two five-membered cyclic monothiocarbonate groups, a compound B) with at least two amino groups, selected from primary or secondary amino groups and optionally a compound C) which at least one functional group that reacts with a group —SH In case of the first alternative and a two-step reaction is only possible if compound C) is used; in such case compounds A), B) are reacted to obtain an intermediate product and the intermediate product is mixed with compound C) to obtain a curable mixture comprising the intermediate product and C).

In case of the second alternative and a one-step reaction all compounds are mixed to obtain a curable mixture comprising a compound A) with at least two five-membered cyclic monothiocarbonate groups or a mixture of a compound A) with a compound A1) with one five-membered cyclic monothiocarbonate group and a compound B) with at least two amino groups, selected from primary or secondary amino groups or a compound B1) with one amino group selected from primary or secondary amino groups or mixtures of compounds B) and B1) and a compound C) with at least two functional groups that react with a group —SH or in case of a carbon-carbon triple bond as functional group that react with a group —SH, with at least one carbon-carbon triple bond.

In case of the second alternative and a two-step reaction, compounds A) or a mixture of compounds A) and A1) are reacted with compounds B), B1) or mixtures thereof to obtain an intermediate product and the intermediate product is mixed with compound C) to obtain a curable mixture comprising the intermediate product and compound C).

In a preferred embodiment of the second alternative a mixture of compound A) and A1) are used. The mixture of A) and A1) may comprise, for example, 1 to 99% by weight of A) and 99 to 1% by weight of A1), based on the weight sum of A) and A1). In a preferred embodiment the mixture comprises at least 10% to 90% by weight of A) and 90 to 10% of A1) based on the weight sum of A) and A1).

Preferably, the mixture is a solution of compound A) which is usually solid under normal conditions (21° C., 1 bar) in compound A1) which is usually a liquid under normal conditions. Such solutions preferably comprise 1 to 60%, notably 5 to 50% and more preferably 10 to 40% by weight of A) and 99 to 40, notably 95 to 50 and more preferably 90 to 60% by weight of A1).

For storage compounds A), A1), B), B1) and C) may be kept separately. In case of both alternatives it is possible to have a two-component curable system whereby the first component comprises the compounds B) and/or B1), only, and the second component comprises all other compounds A), A1) and C).

Preferably, the reactions in case of both alternatives are performed at temperatures of from −20 to 250° C., preferably between 20 and 100° C. This applies to the one-step reaction and to both steps of the two-step reaction. Alternatively, any activation energy for the reactions may be provided by high-energy radiation such as visible or UV-light.

The one-step or two-step reaction may be performed with solvent. The use of a solvent might be helpful, in case that at least one of the compounds A), B) and C) is solid and other liquid compounds A), A1), B), B1) or C) do not act already as solvent for the solid compound, for example in case of the above solution of A) in A1). Suitable solvents are, for example, ethylacetate, butylacetate, methyl ethyl ketone, dioxane, methanol, ethanol, water, tetrahydrofuran and dimethylformamide. It is an advantage of the process that usually no additional solvent is required as usually at least one of the compounds A), B) and C) is liquid and serves already as solvent.

Furthermore, the above described curable compositions of A), A1), B), B1) and C) or the separate compositions in case of a two component curable systems may comprise further additives, for example catalysts or inhibitors or additives which are necessary or desired for the intended use of the polymer obtained.

Catalysts may, for example, be used in case of compounds C) that add via an addition reaction to the groups —SH. Addition reactions may follow an ionic or a radical mechanism. The ionic mechanism usually requires the presence of a basic compound as catalyst. The basic catalyst may be compound B) or B1) itself. In case of an addition to ethylenically unsaturated groups the presence of compound B) or B1) is often sufficient. In case of epoxy groups as functional groups preferably a basic catalyst such as a tertiary amine, for example Versamin® is added. Such catalysts are usually used in an amount of 0.1 to 3 mol catalyst per one mol of epoxy groups. Other catalysts may be amidine or guanidine based systems or phosphines A radical mechanism of the addition reaction is supported by initiators that form radicals. Such initiators are either thermal, redox, electrochemical or photoactive initiators well known from radical polymerization.

Furthermore, the above curable compositions of A), A1), B), B1) and C) or the separate compositions in case of a two component curable systems may comprise stabilizers. Such stabilizers might be helpful to avoid decomposition or early polymerization in case of long time storage or transport of the compositions.

In particular redox stabilizers that reduce or avoid oxidation of S—H groups which is a side reaction may be added.

Oxidation of S—H groups may lead to disulfide bridges between neighbored molecules thus reducing the amount of S—H groups available for the reaction with compound C. An example of such stabilizer is Tris(2-carboxyethyl)phosphin (TCEP).

Alternatively, any additives or stabilizers may also be added after the reaction to the polymer obtained.

In the above reactions further reactive compounds may be used, for example compounds A1) and/or B1) in case of the first alternative or compounds with only one functional group that reacts with a group —SH in case of the second alternative. Such compounds are used, for example, as modifier which might limit the molecular weight of the polymer obtained. In a preferred embodiment, the polymer obtained by the process of this invention consists to at least 60% notably to at least 80% by weight of compounds A), B) and optionally C) in case of the first alternative and consists to at least 60% notably to at least 80% by weight of compounds A), A1), B), B1) and C) in case of the second alternative. In a more preferred embodiment the polymer obtained by the process of this invention consists to at least 90% notably to at least 95%, respectively to at least 98% by weight of compounds A), B) and optionally C) in case of the first alternative and consists to at least 90% notably to at least 95%, respectively to at least 98% by weight of compounds A), A1), B), B1) and C) in case of the second alternative.

The obtained polymers are usually transparent, non-tacky and solid at room temperature.

The process of this invention provides an alternative method for the manufacturing of polymers with urethane groups. In this process the use of compounds with isocyanate groups is avoided. The process of this invention is an easy and effective manufacturing process, notably a process not requiring high energy or high temperatures. Solid and transparent polymers are easily available and are useful for a variety of technical applications such as coatings, adhesives, thermoplastic or duroplastic material for the formation of molds in any form. Hybrid polymers are available with modified properties due to the introduction of urethane groups in polymers such as epoxy resins. Optical polymers with high refractive index are accessible. Polymers obtained show high thermal stability. The process furthermore offers a curing mechanism for low temperature curing which is compatible with the presence of oxygen.

EXAMPLES

Compounds with five-membered cyclic monothiocarbonate groups.

Following compounds with five-membered cyclic monothiocarbonate groups have been used in the examples:

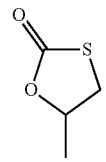

methyl monothiocarbonate

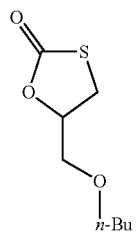

n-butylglycidyl-monothiocarbonate

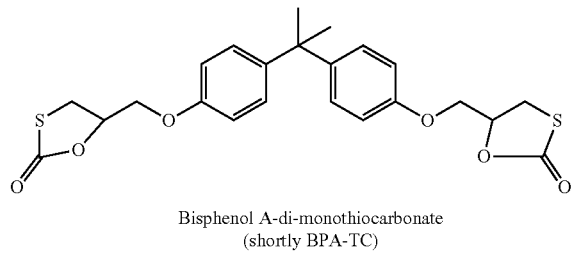

Bisphenol A-di-monothiocarbonate
(shortly BPA-TC)

Synthesis Examples 1 to 6 for Compounds with Five-Membered Cyclic Monothiocarbonate Groups First Step: Synthesis of β-Chloro Alkylchlorformates Epoxide was charged to a reactor and kept at −30° C. The molar amount of epoxide is listed in Table 1. 0.01 mol of tetra(n-butyl ammonium chloride were added per 1 mol of epoxide. Thereafter phosgene is added slowly as the reaction is exothermic. When adding the phosgene the temperature was kept via cooling at the temperature listed in the Table. The time of metering phosgene is listed in the Table. The total amount of phosgene was 1.1 mol per 1 mol of epoxide. When the addition of phosgene was completed the reaction mixture was further stirred for about (2 hours). Unreacted phosgene was removed by nitrogen stripping. No further work-up was necessary. The obtained β-chloro alkylchlorformates could be used directly in the next step which is the formation of the thiocarbonates.

The epoxide, the obtained β-chloro alkylchlorformates and further details of the reaction are listed in Table 1.

The β-chloro alkylchlorformates are obtained in form of two different structural isomers (stereoisomers) a and b

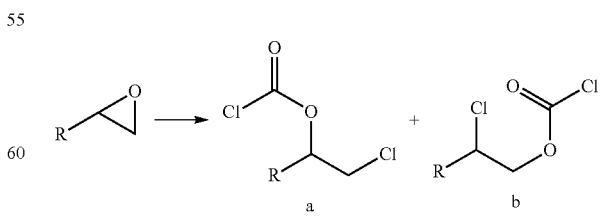

The selectivities regarding a and b are listed in the Table 1 as well. The total yield listed in Table 1 is based on the epoxide used as starting material.

| Synthesis example | epoxide | β-chloro alkylchlorformates | T [° C.] | selectivity a:b | total yield (a + b) [%] |
|---|---|---|---|---|---|
| 1 | (methyloxirane) (1.6 mol) | Cl-C(=O)-O-CH(CH₃)-CH₂Cl | 15-20 | 90:10 | >99 |
| 2 | Cl-CH₂-(oxirane) (2.5 mol) | Cl-C(=O)-O-CH(CH₂Cl)-CH₂Cl | 15-20 | 98.5:1.5 | 97 |
| 3 | BuO-CH₂-(oxirane) (1.0 mol) | Cl-C(=O)-O-CH(CH₂OBu)-CH₂Cl | 15-20 | 96:4 | 96 |
| 4 | RO-CH₂-(oxirane) R = C12/C14-n-Alkyl (0.33 mol Epoxid) | Cl-C(=O)-O-CH(CH₂OR)-CH₂Cl R = C12/C14-n-Alkyl | 15-30 | >98 | >99 |
| 5 | Bisphenol A diglycidyl ether (0.4 mol) | Bis(β-chloroalkyl chloroformate) from BPA diglycidyl ether | 35-40 | ca. 95:5 | >99 |
| 6 | Polyethylenglycol-diglycidylether, Araldite DY3602 (n = ca. 5) (1 mol Epoxid-Äq.) | corresponding bis-β-chloroalkyl chloroformate | 10-20 | >95:5 | >99 |

In case of synthesis example 5 und 6 the yield and selectivity was determined by 1H- und 13C-NMR.

Second Step: Synthesis of Monothiocarbonates

Synthesis of Substituted Cyclic Mono-Thiocarbonates:

The respective β-chloroalkyl chloroformate from synthesis examples 1 to 4 (50 g) and dichloromethane (50 mL) are placed in a 500 mL 4 neck round bottom flask equipped with a KPG crescent stirrer, dropping funnel, thermometer and a reflux condenser. The solution was cooled down to 0° C. with an ice bath before Na₂S (1 equiv., 15 wt % aqueous solution) was slowly added, maintaining the temperature at 5° C. After the complete addition the ice bath was removed and the reaction mixture allowed to warm to room temperature. After stirring for 4 h the phases were separated and the aqueous phase was extracted with dichloromethane (2×50 mL). The solvent was removed from the combined organic phases under reduced pressure and the residual liquid purified by (Kugelrohr) distillation, yielding the desired cyclic thiocarbonate.

TABLE 2

Selectivities and isolated yields (purities in brackets) of the various monothiocarbonates

| β-chloro alkylchlor-formates from synthesis example | monothio-carbonate obtained | Area % of GC peak of monothio-carbonate in relation to area of all GC peaks | yield of monothio-carbonate and purity after distillation in brackets |
|---|---|---|---|
| 1 | Methyl | 84% | 69% (größer 97%) |
| 2 | Methylene chloride | 86% | 77% (größer 95%) |
| 3 | C₄-Glycidyl | 92% | 83% (>97%) |
| 4 | C₁₂/C₁₄-Glycidyl | 66% | 20% (80%) |

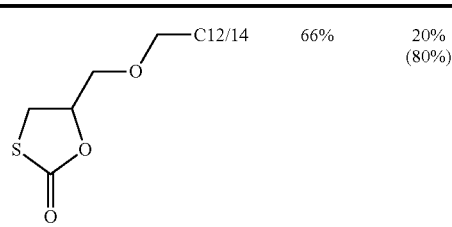

Synthesis of Compounds with Two Cyclic Monothiocarbonate Groups:

The respective bis-β-chloroalkyl chloroformiate (50 g) and dichloromethane (50 mL) are placed in a 500 mL 4 neck round bottom flask equipped with a KPG crescent stirrer, dropping funnel, thermometer and a reflux condenser. The solution was cooled down to 0° C. with an ice bath before Na₂S (2 equiv., 15 wt % aqueous solution) was slowly added, maintaining the temperature at 5° C. After the complete addition the ice bath was removed and the reaction mixture allowed to warm to room temperature. After stirring for 2 h the phases were separated and the aqueous phase was extracted with dichloromethane (2×50 mL). The solvent was removed from the combined organic phases under reduced pressure yielding the desired compound with two cyclic monothiocarbonate groups.

TABLE 3

Selectivities and purities of the various compounds with two cyclic mono-thiocarbonate groups

| β-chloro alkylchlor-formates from synthesis example | monothiocarbonate | area % of GC peak of monothiocarbonate in relation to area of all GC peaks |
|---|---|---|
| 5 | Bisphenol A-TC | 80% |

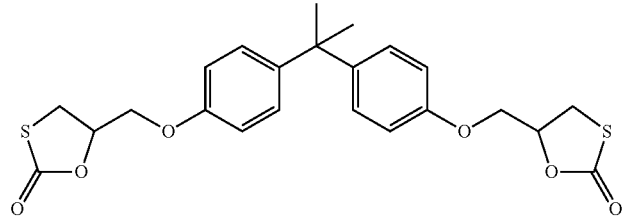 [SMILES: CC(C)(c1ccc(OCC2CSC(=O)O2)cc1)c1ccc(OCC2CSC(=O)O2)cc1]

TABLE 3-continued

Selectivities and purities of the various compounds with two cyclic mono-thiocarbonate groups

| β-chloro alkylchlor- formates from synthesis example | monothiocarbonate | area % of GC peak of monothiocarbonate in relation to area of all GC peaks |
|---|---|---|
| 6 | 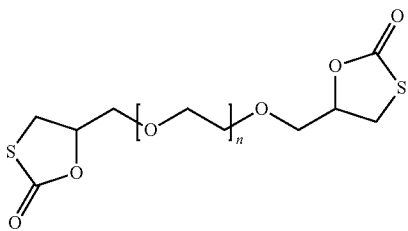<br>PEGG | >99% |

Preparation of Polymers

Polymer Example 1: Polymer of Compound A) and B)

To a solution of 1.0 g Bisphenol A dithiocarbonate BPA-TC in 2 g of tetrahydrofuran (THF) 0.23 g of pentamethylene diamine were added. The mixture was stirred at room temperature and subsequently poured in an aluminum mold (diameter 6.5 cm).

Curing was achieved at room temperature (24 h) followed by post curing at 60° C. (4 h). The resulting polymer was further characterized by DSC (glass transition temperature, Tg).

Polymer Example 2: Polymer of A), B) and C)

A solution of 1.0 g BPA-TC in 2 g of THF was mixed with 0.54 g of butandiol dimethacrylate. To the resulting mixture 0.23 g of pentamethylene diamine were added. The mixture was stirred at room temperature and subsequently poured in an aluminum mold (diameter 6.5 cm).

Curing was achieved at room temperature (24 h) followed by post curing at 60° C. (4 h). The resulting elastic polymeric film was further characterized by DSC (glass transition temperature, Tg).

Polymer Example 3: Polymer of A), B1) and C)

A solution of 1.0 g Bisphenol A dithiocarbonate (BPA-TC) in 2 g of THF was mixed with 0.54 g of butandiol dimethacrylate and 0.008 g of Tris(2-carboxyethyl)phosphine hydrochloride (stailizer). To the resulting mixture 0.58 g of octylamine were added. The mixture was stirred at room temperature and subsequently poured in an aluminum mold (diameter 6.5 cm).

Curing was achieved at room temperature (24 h) followed by post curing at 60° C. (4 h). The resulting viscous liquid was further characterized by DSC (glass transition temperature, Tg).

Polymer Example 4: Polymer of A), B1) and C)

A solution of 1.0 g BPA-TC in 2 g of THF was mixed with 0.51 g of trimethylolpropane trimethacrylate. To the resulting mixture 0.58 g of octylamine were added. The mixture was stirred at room temperature and subsequently poured in an aluminum mold (diameter 6.5 cm). Curing was achieved at room temperature (24 h) followed by post curing at 60° C. (4 h). The resuiting polymeric film was further characterized by DSC (glass transition temperature, Tg).

TABLE 4 glass transition temperatures (Tg) of polymers obtained

| Polymer of polymer example | Tg [° C.] |
|---|---|
| 1 | 50.6 |
| 2 | 6.9 |
| 3 | −22.8 |
| 4 | −4.2 |

Polymer Example 5: Polymer of A), A1), B) and C)

Under stirring 1 g Bisphenol A dithiocarbonate (0.00217 mol) were dissolved in n-butylglycidylmonothiocarbonate (3.0 g, 0.0157 mol, 1 eq). Trimethylolpropane trimethacrylate (2.26 g) was subsequently added. The mixture was homogenized. To the solution was added 1,5-pentandiamine (1.022 g) via syringe. After 10 second of vigorous stirring at room temperature, the reaction mixture was poured in metal mold (bar-shaped)). The molds were stored at 60° C. for 3 hours and the samples were subsequently released from the molds.

The reaction scheme is as follows:

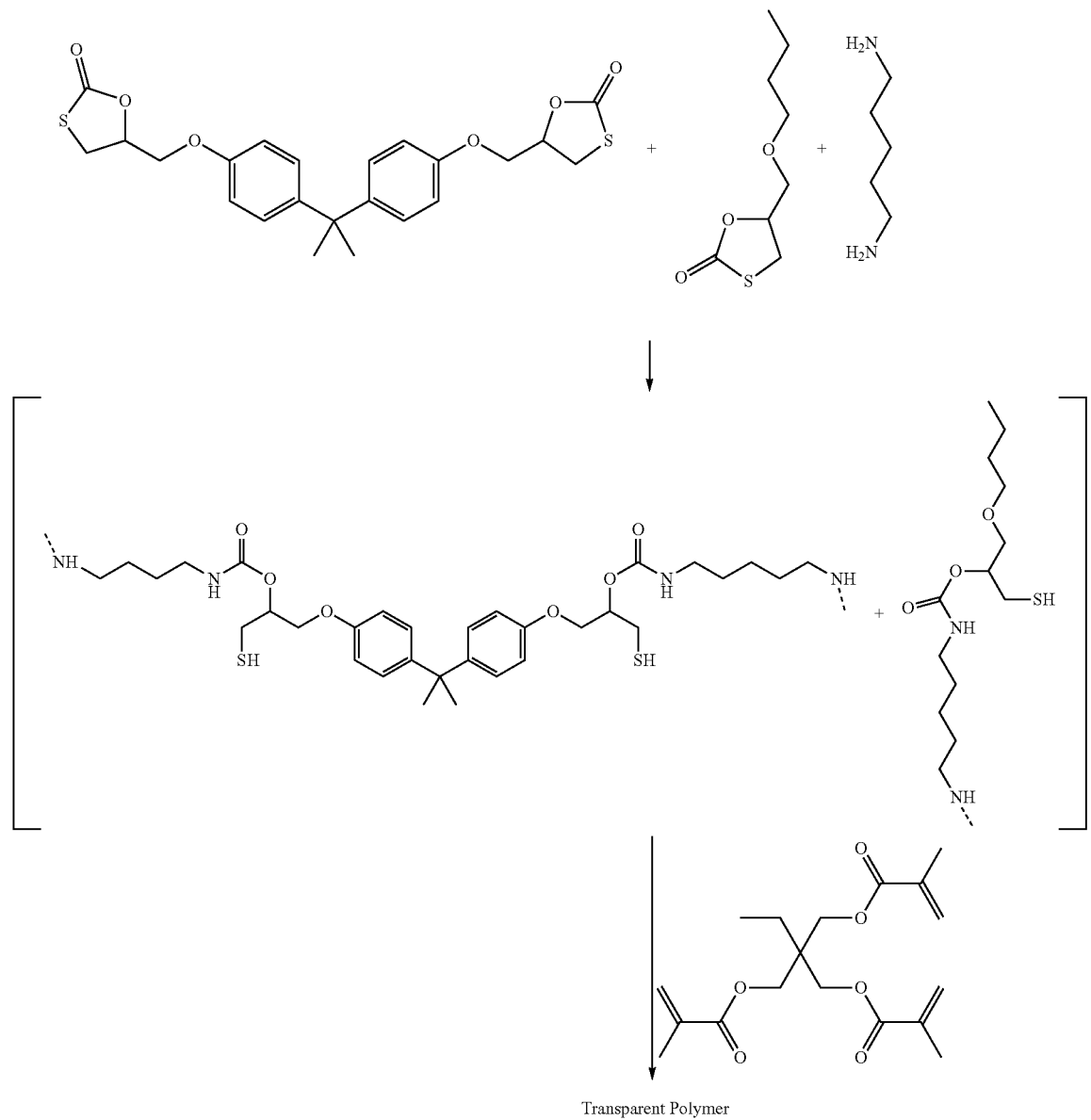

Transparent Polymer

The polymer was obtained as a colorless tack-free solid and as a rigid bar showing high transparency.

Polymer Example 6 polymer of A), A1), B) and C
Bisphenol a Dithiocarbonate (BPA-Dithiocarbonate) and n-Butylglycidyl-Monothiocarbonate, Triamine and Compound C with Double Bond In a 50 ml flask fitted with a magnetic stirrer 5-(buthoxymethyl)-1,3-oxathiolan-2-one (2.4 g) was combined with trimethylolpropane-trimethacrylat, (1.72 g) and BPA-Dithiocarbonate (0.6 g) and subsequently homogenized. To the stirred solution was rapidly added Tris(2-aminoethyl)amine (0.95 g). The mixture was stirred and homogenized at room temperature. The temperature increased from 25 to 40° C. within 60 seconds and the polymer was cured within 30 min.

Example 7 polymer of A), A1), B) and C
Bisphenol a Dithiocarbonate (BPA-Dithiocarbonate) and n-Butylglycidyl-Monothiocarbonate, Triamine and Compound C with Epoxy Groups In a 50 ml flask fitted with a magnetic stirrer a mixture of 1,4 dioxane (0.5 g), 5-(buthoxymethyl)-1,3-oxathiolan-2-one (0.48 g) and BPA-Dithiocarbonate (1.15 g) was homogenized at 30° C. and subsequently combined with trimethylolpropane-triglycidylether (0.76 g). After cooling to room temperature to the stirred solution was rapidly added Tris (2-aminoethyl)amine (0.28 g).

The temperature increased and the polymer solidified within 30 min.

Example 8 polymer of A) and B)
Polyethyleneglycol-Dithiocarbonate (PEG-Dithiocarbonate) and Diamine without Compound C In a 50 ml flask fitted with a magnetic stirrer PEG-Dithiocarbonate (average MW: 620 g/mol, 5,0 g) was combined with 1,3-Bis(aminomethyl)cyclohexane (1.15 g) The temperature increased from 25 to 38° C. within 240 seconds and the polymer solidified within 18 h

The invention claimed is:

1. A process for the manufacturing of a polymer with urethane groups, comprising, in a first alternative:
   reacting
   a compound A) with at least two five-membered cyclic monothiocarbonate groups,
   a compound B) with at least two amino groups, selected from primary or secondary amino groups,
   and
   optionally a compound C) with at least one functional group that reacts with a group —SH;
   or in a second alternative:
   reacting
   a compound A) with at least two five-membered cyclic monothiocarbonate groups or a mixture of a compound A) with a compound A1) with one five-membered cyclic monothiocarbonate group,
   a compound B) with at least two amino groups, selected from primary or secondary amino groups or a compound B1) with one amino group selected from primary or secondary amino groups or mixtures of compounds B) and B1) and
   a compound C) with at least two functional groups that react with a group —SH or in case of a carbon-carbon triple bond as functional group that react with a group —SH, a compound C) with at least one carbon-carbon triple bond,
   wherein, in the first alternative or in the second alternative, the compound A) is a compound of formula I:

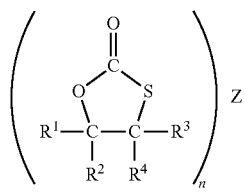

(I)

wherein $R^1$ or $R^2$ is a linking group to Z,
three of the groups $R^1$ to $R^4$ are hydrogen,
n is an integral number of at least 2, and
Z is an n-valent organic group.

2. The process according to claim 1, wherein the linking group is simply a bond or a group $CH_2$—O— or $CH_2$—O—C(=O)—.

3. The process according to claim 1, wherein Z is a n-valent organic group with up to 50 carbon atoms and may comprise oxygen and n is an integral number from 2 to 5.

4. The process according to claim 1, wherein n is 2.

5. The process according to claim 1, wherein Z is a polyalkoxylene group of formula G1:

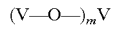 (G1)

wherein V represents a C2-to C20 alkylen group and m is an integral number of at least 1, and whereby the terminal alkylene groups V are bonded to the linking group, which is one of the groups $R^1$ to $R^2$.

6. The process according to claim 1, wherein Z is a group of formula G2:

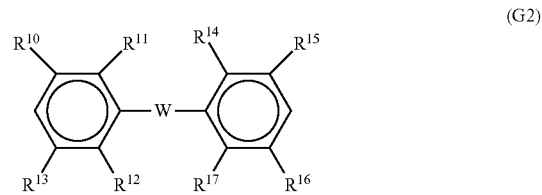

wherein W is a bi-valent organic group with at maximum 10 carbon atoms and $R^{10}$ to $R^{17}$ independently from each other represent H or a C1- to C4 alkyl group and wherein the two hydrogen atoms in the para position to W are replaced by the bond to the linking group, which is one of the groups $R^1$ to $R^2$.

7. The process according to claim 1, wherein Z is a group G3 which is an alkylene group.

8. The process according to claim 1, wherein compound B is a compound B) with at least two aliphatic or cycloaliphatic primary amino groups.

9. The process according to claim 1, wherein compound C) is present and wherein the functional group of compound C) that reacts with —SH is selected from non-aromatic, ethylenically unsaturated groups, epoxy groups, isocyanate groups, groups with a non-aromatic carbon-nitrogen double bond, carbonyl groups or halides.

10. The process according to claim 9, wherein compound C) is present and wherein the functional group of compound C) that reacts with —SH is selected from non-aromatic, ethylenically unsaturated groups or epoxy groups.

11. The process according to claim 9, wherein compound C) is present and wherein the functional group of compound C) that reacts with —SH is a methacryl group.

12. The process according to claim 1, wherein in the second alternative a solution of compound A) and A1) is used.

13. The process according to claim 1, wherein in both alternatives the reaction is carried out in one step by reacting all compounds simultaneously.

14. The process according to claim 1, wherein in both alternatives the reaction is carried out in two steps,
   in the first alternative ley first reacting A) and B) and then reacting the obtained intermediate with C), and
   in the second alternative by first reacting A) or mixtures of A) and A1) and B) or B1) or mixtures of B) and B1) and then reacting the obtained intermediate with C).

15. A polymer with urethane groups obtained by a process according to claim 1.

16. A curable composition comprising:
   a compound A) with at least two five-membered cyclic monothiocarbonate groups,
   a compound B) With at least two a o groups, selected from primary or secondary amino groups, and optionally
   a compound C) which at least one functional group that reacts with a group —SH;

or comprising the reaction product of the two compounds A) and B) and, in addition, C),
wherein the compound A) is a compound of formula I:

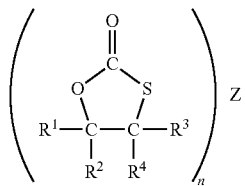
(I)

wherein $R^1$ or $R^2$ is a linking group to Z,
three of the groups $R^1$ to $R^4$ are hydrogen,
n is an integral number of at least 2, and
Z is an n-valent organic group.

17. A curable composition comprising:
a compound A) with at least two five-membered cyclic monothiocarbonate groups or a mixture of a compound A) with a compound A1) with one five-membered cyclic monothiocarbonate group,
a compound B) with at least two amino groups, selected from primary or secondary amino groups or a compound B 1) with one amino group selected from primary or secondary amino groups or mixtures of compounds B) and B1), and
a compound C) with at least two functional groups that react with a group —SH or in case of a carbon-carbon triple bond as functional group that react with a group —SH, with at least one carbon-carbon triple bond;
or comprising the reaction product of the compounds A) or the mixture of A) and A1) and B) or B1) or the mixture of B) and B1) and, in addition, C),
wherein the compound A) is a compound of formula I:

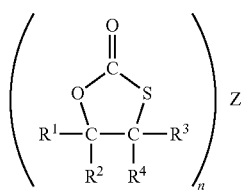
(I)

wherein $R^1$ or $R^2$ is a linking group to Z,
three of the groups $R^1$ to $R^4$ are hydrogen,
n is an integral number of at least 2, and
Z is an n-valent organic group.

18. A compound of formula I

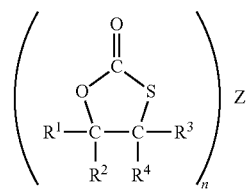

wherein $R^1$ or $R^2$ is a linking group to Z,
three of the groups $R^1$ to $R^4$ are hydrogen,
n is an integral number of at least 2, and
Z is a n-valent organic group.

19. A process for the manufacturing of a polymer with urethane groups, comprising, in a first alternative:
reacting
a compound A) with at least two five-membered cyclic monothiocarbonate groups,
a compound B) with at least two amino groups, selected from primary or secondary amino groups,
and
a compound C) with at least one non-aromatic, ethylenically unsaturated functional group that reacts with a group —SH;
or in a second alternative:
reacting
a compound A) with at least two five-membered cyclic monothiocarbonate groups or a mixture of a compound A) with a compound A1) with one five-membered cyclic monothiocarbonate group,
a compound B) with at least two amino groups, selected from primary or secondary amino groups or a compound B1) with one amino group selected from primary or secondary amino groups or mixtures of compounds B) and B1) and
a compound C) with at least two non-aromatic, ethylenically unsaturated functional groups that react with a group —SH or in case of a carbon-carbon triple bond as functional group that react with a group —SH, a compound C) with at least one non-aromatic carbon-carbon triple bond.

20. The process of claim 1, wherein the polymer is free of thiourethane groups.

* * * * *